United States Patent [19]
Nukui et al.

[11] Patent Number: 5,167,450
[45] Date of Patent: Dec. 1, 1992

[54] CALORIMETER

[75] Inventors: Kazumitu Nukui, Kanagawa; Naoki Matubara, Tokyo, both of Japan

[73] Assignees: Tokyo Gas Co., Ltd.; Oval Engineering Co., Ltd., both of Tokyo, Japan

[21] Appl. No.: 713,233

[22] Filed: Jun. 10, 1991

[30] Foreign Application Priority Data

Aug. 2, 1990 [JP] Japan .................. 2-205378

[51] Int. Cl.$^5$ ............................................. G01N 25/20
[52] U.S. Cl. ........................................ 374/31; 374/36; 364/556
[58] Field of Search ................. 374/36, 37, 40, 41, 374/31; 364/556, 557

[56] References Cited
U.S. PATENT DOCUMENTS
4,384,792 5/1983 Sommers et al. .................. 374/36

Primary Examiner—William A. Cuchlinski, Jr.
Assistant Examiner—W. Morris Worth
Attorney, Agent, or Firm—Jordan and Hamburg

[57] ABSTRACT

A calorimeter comprises a laminar flow type flowmeter for measuring the volume of flow of a fuel gas as a value proportional to the difference between the pressures of the laminar flow elements and a stream pipe serially connected to the laminar flow type flowmeter to create a laminar flow therethrough. The stream pipe is provided with a heating means, a temperature sensing means for detecting the difference between the temperatures of the fuel's flow to and from the stream pipe portion heated by the heating means, and a thermal-type flowmeter for measuring a mass flow proportional to the differential temperature sensed. A computer unit calculates the outflow pressure and the volume of flow of the fuel gas in its normal state from the measured values of the absolute pressure, the differential pressure and the temperature of the fuel gas flowing into the laminar flow-type flowmeter and calculates the calorific value of the fuel gas as a value that is negatively proportional to the differential pressure.

4 Claims, 5 Drawing Sheets

CALORIMETER

BACKGROUND OF THE INVENTION

The present invention relates to a calorimeter and, more particularly, to a simple calorimeter wherein a thermal type flowmeter and a laminar flow-type flowmeter are serially connected to one another to detect a loss of pressure in the mixed fuel gas in a normal state at the outlet of said laminar flow-type flowmeter on the condition that the output of the thermal-type flowmeter is kept at a constant value and to determine the calorific value of the mixed fuel gas as a function of the lost pressure.

It is regulated by law that fuel gas and natural gas, before being forwarded from a manufacturing works, shall be measured for their calorific values and combustability, and that calorimeters to be used for measuring the calorific values of a mixed gas also shall comply with the specified requirements.

A typical example is the Junker's flow-type calorimeter which completely burns a sample of mixed fuel gas with air and then cools the combustion product (waste gas) to the initial temperature thereby bringing the by-produced water vapor into a liquid state and causing the total amount of generated heat to be absorbed by the water, thereby multiplying the current water flow to correspond to a certain amount of mixed gas sample by the difference between the temperatures of said water at its inlet and outlet in order to get a product from which a total calorific value is calculated. This calorimeter is used as a standard instrument, but in application it requires such severe surrounding conditions that the difference between the room's temperature and the water's temperature must be kept at the constant temperature of ±0.5° C. and the change in the water's temperature during one measurement shall not be more than 0.05° C. and, furthermore, there is a poor response time. Therefore, the calorimeter is suitable for accuracy tests but not suitable for use in a production line. Consequently, it is also possible to apply quick-response calorimeters which are normally used for continuously measuring calorific values of fuel gas products before being forwarded from the manufacturing works. The quick-response calorimeters are such that fuel gas and air are respectively measured and then mixed with one another, the mixture being burned by the use of a burner, the temperature of the waste gas produced and temperature of the air at the burner's inlet are detected respectively by the use of temperature sensors, e.g. by thermo-couples, the difference between the temperatures and the specific gravity of the fuel gas in relation to the air are detected respectively, the Woppe's index (hereinafter referred to as W.I) which is a ratio of a total calorific value of the sample gas to the square root of the specific gravity of the sample gas relative to air is calculated, the calorific value of the sample gas is determined as a product of the W.I. and the square root of the specific weight of the sample gas relative to air. Another measuring method is to calculate the calorific value of the mixed gas from the result of the measurement of its density based upon the results of experiments showing the proportional relation between the calorific value and the density of the mixed gas.

The above-mentioned quick-response type calorimeters, usable in place of the standard Junker's flow-type gas calorimeter, have the drawback that when they have been operating for a long time, the accuracy of the measurements is decreased thereby requiring the correction of the measured value to twice the continuous cycle of operation. This correction work is complicated and not easy to do. The drawback of the densitometric method is that since the applicable density meter is expensive, it is impossible to provide a low cost and simple means for measuring the calorific values of the fuel gas.

SUMMARY OF THE INVENTION

It is an object of the present invention to provide a simple and accurate calorimeter in which a thermal-type flowmeter and a laminar flow-type flowmeter are combined with each other to realize an easier and more accurate measurement of the calorific value of the fuel gas, utilizing the fact that the mixed gas has a calorific value that is proportional to its density and negatively proportional to its specific heat at a constant pressure and also to its viscosity.

It is another object of the present invention to provide a calorimeter capable of measuring the calorific value of a mixed fuel gas with a higher accuracy and by simpler means with no effect or variation in the flow conditions by virtue of the possibility of converting the volume of flow of the fuel gas measured by a laminar flow-type flowmeter into the flow in normal conditions.

It is another object of the present invention to provide a simple and low-cost calorimeter which, by virtue of the adoption of a thermostatic chamber that is a good heat conductor with a reduced variation of the inner temperature, is capable of measuring stably the calorific values of the mixed fuel gas and is suitable for use as an auxiliary measuring means for a standard calorimeter.

DESCRIPTION OF THE PREFERRED EMBODIMENTS

Fuel gas which is used as today's city gas is first prepared as a liquified natural, gas (hereinafter referred to as LNG) with a high calorie hydrocarbon gas (e.g. propane or butane) added thereto to obtain the required calorific value. Namely, since LNG produced in different districts may differ from one another in the content of methane gas being the main component, i.e. in calorific value, how much propane or butane gas mixed with each LNG product is regulated. The calorific value of the mixed gas depends upon its density ($\rho$), specific heat (Cp) at a constant pressure (hereinafter referred to as "specific heat") and viscosity ($\mu$).

Figure 1:
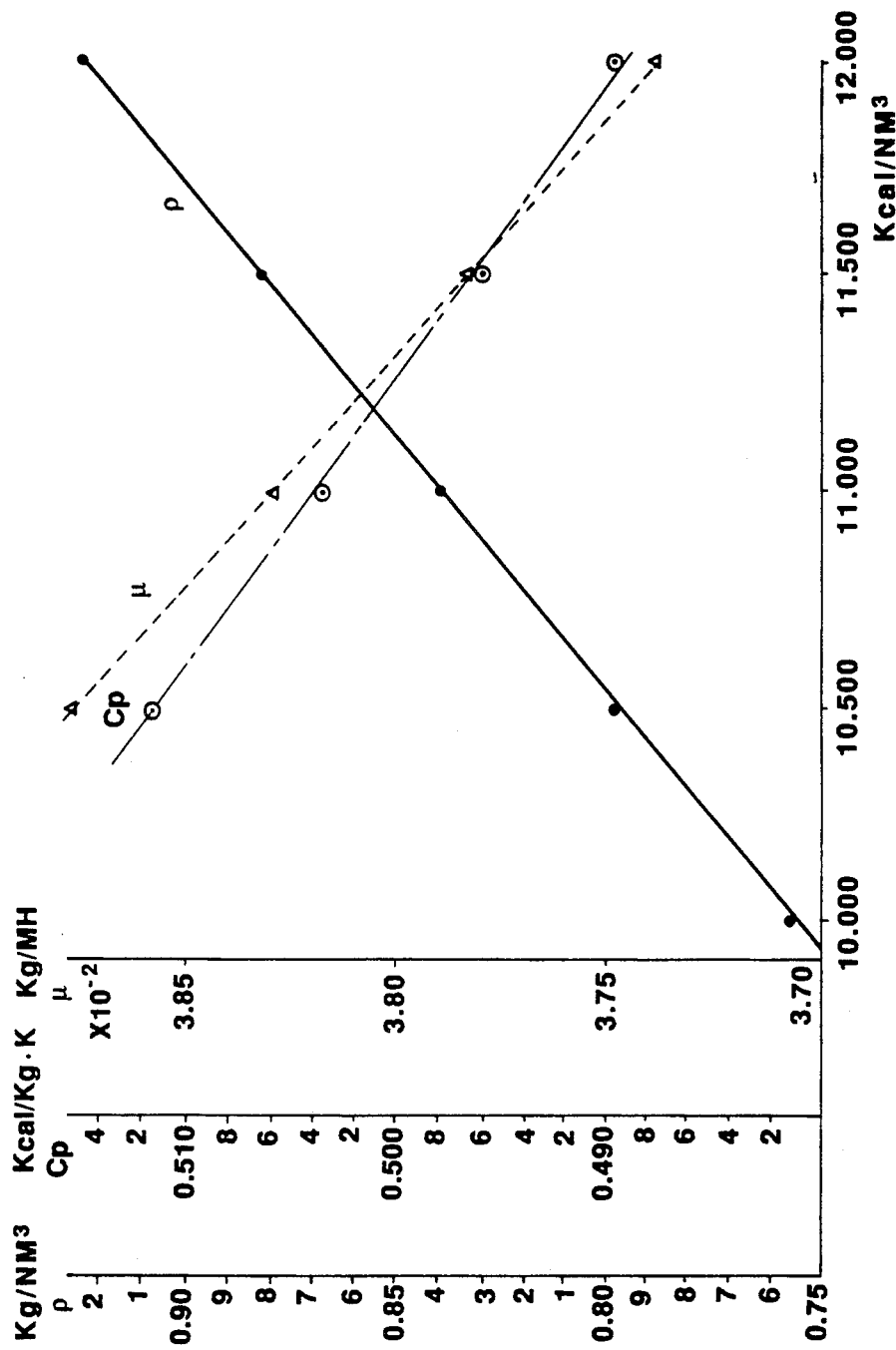
FIG. 1 is a graph showing the relation between the physical properties and calorific values of a fuel gas.

Referring to FIG. 1, the measured calorific value of a fuel gas is plotted along the abscissa and the measured values of density ($\rho$); the specific heat (Cp) and viscosity ($\mu$) are plotted along an ordinate; and the resulting curves indicate a relationship between the physical properties and the calorific values of the fuel gas. It may be appreciated from the graph that the calorific value of the mixed gas is a linear function of the density, the specific heat and the viscosity respectively.

Figure 2:
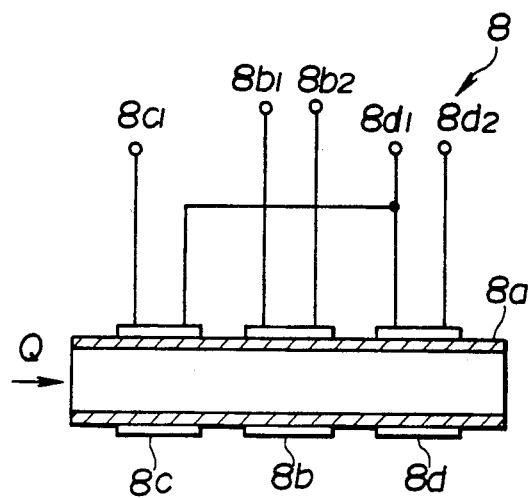
FIG. 2 is an illustration for explaining the operating principle of a thermal-type flowmeter.

FIG. 2 shows a principal construction of a thermal-type flowmeter 8. In FIG. 2, 8a is a stream pipe of high thermal conductivity wherein a fluid, e.g. fuel gas having its density "$\rho$" and specific heat "Cp" flows in layers without turbulence at a Reynolds number of no more than 200 and at a flowrate "Q" in the direction shown by an arrow, and 8b is a heater composed of a resistance wire wound around the center portion of the stream pipe. The heater has terminals $8b_1$ and $8b_2$ wherethrough a constant heating power is supplied. Resistance wires 8c and 8d are wound around the stream pipe so as to be located respectively forward and backward from the heater 8b. Both resistance wires have the same resistance value at the flowrate Q of 0 and form two arms 8c and 8d of a bridge circuit which can detect a variation in the resistance value depending upon the thermal conductivity of the flow as a voltage value proportional to the mass flow. $8c_1$, $8d_1$ and $8d_2$ designate terminals of the bridge circuit (not shown). Since in the thermal-type flowmeter a transfer of heat from the stream pipe wall 8a to the fluid occurs at the boundary layers of the laminar flow, and its value is proportional to the laminar boundary layer's thickness, it is known that the output voltage V of the bridge circuit at a proportionality constant $K_1$ can be expressed as follows:

$$V = K_1 C p \rho Q \ldots \quad (1)$$

For fluid having a known specific heat Cp the output voltage V can be obtained as a value that is proportional to its mass flowrate $\rho Q$.

Figure 3:
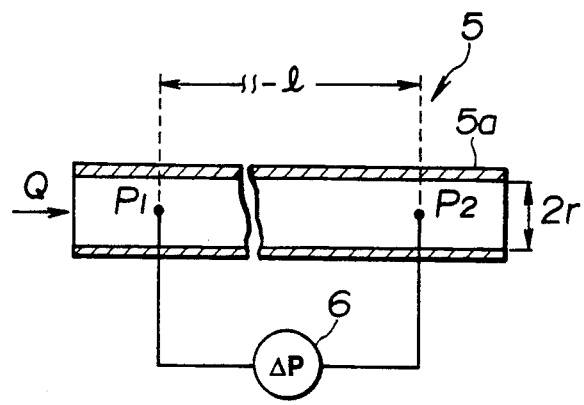
FIG. 3 is an illustration for explaining the operating principle of a laminar flow-type flowmeter.

FIG. 3 shows the operating principle of a laminar flow type flowmeter 5. In FIG. 3, 5a is a stream pipe with the radius "$\gamma$" and the length "l" wherein fluid flows in layers at the flowrate Q and 6 is a differential pressure gauge for measuring the differential pressure $\Delta P$ between the inlet pressure $P_1$ and the outlet pressure $P_2$ of the laminar flow-type flowmeter.

According to the Hagen-Poiseuille equation, the flow rate Q of the fluid is expressed as follows:

$$Q = \frac{\pi \gamma^4}{16 \mu l} \frac{(P_1 - P_2)(P_1 + P_2)}{P_1} \quad (2)$$

$$= \frac{K_2}{\mu} \cdot \Delta P \left(1 + \frac{P_2}{P_1}\right)$$

where $\frac{\pi \gamma^4}{16 l} = K_2$ and $\mu$ represent the viscosity of the gas.

In the case where fuel gas flows through the laminar flow-type flowmeter 5 and the thermal type flowmeter 8 which are serially connected to each other, it is possible to put the equation (2) in the place of Q in the equation (1) to get the following equation (3).

$$V = K_1 K_2 \frac{C p \rho}{\mu} \Delta P \left(1 + \frac{P_2}{P_1}\right) \quad (3)$$

On the other hand, from the functional relation between the properties and the calorific value of the fuel gas, which is shown in FIG. 1, the following equations can be obtained:

(a) The relation between the density $\rho$ and the calorific value H of the fuel gas:

$$\rho = K_3 H (K_3 \text{ is a constant}) \ldots \quad (4)$$

(b) The relation between the specific heat Cp and the calorific value H of the fuel gas:

$$Cp = -K_4 H (K_4 \text{ is a constant}) \ldots \quad (5)$$

(c) The relation between the viscosity $\mu$ and the calorific value H of the fuel gas:

$$\mu = -K_5 H (K_5 \text{ is a constant}) \ldots \quad (6)$$

If the output V is controlled at a constant value and can be treated as a constant, from the equations (4), (5) and (6) the following equation can be obtained:

$$H = \frac{K}{\Delta P \left(1 + \frac{P_2}{P_1}\right)} \quad (7)$$

Where constant $K = K_5 V / K_1 \cdot K_2 \cdot K_3 \cdot K_4$.

The equation (7) makes it possible to calculate the calorific value H of the fuel gas as a value inversely proportional to the difference $\Delta P$ between the inlet pressure $P_1$ and the outlet pressure $P_2$ of the laminar type flowmeter.

Figure 4:
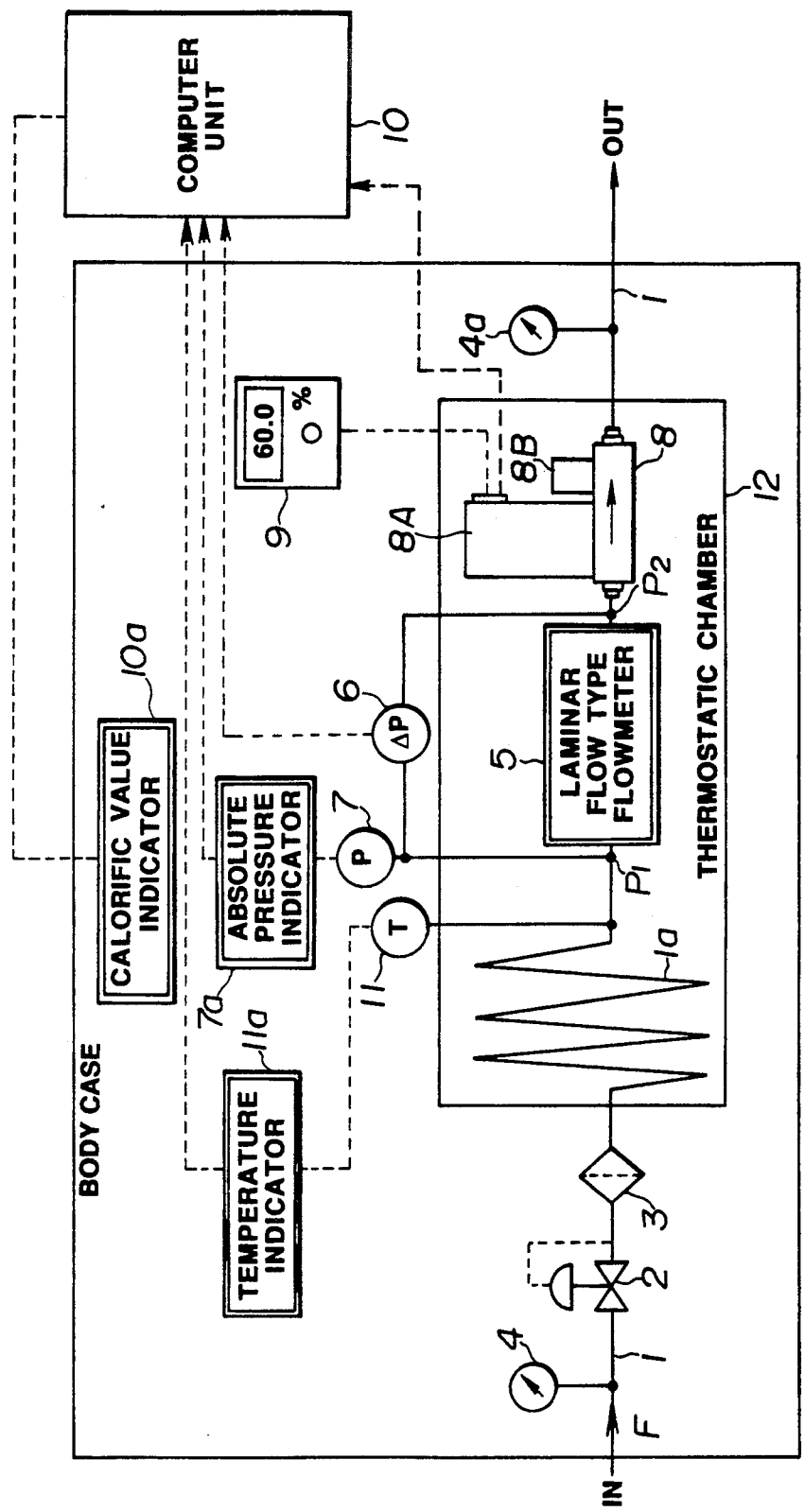
FIG. 4 is an example of a construction of a calorimeter embodied in the present invention.

FIG. 4 shows the construction of a calorimeter, according to the present invention, which embodies the above-mentioned operating principle. In FIG. 4, 1 is a passage for fuel gas to be measured, 2 is a reducing valve for reducing the pressure of the fuel gas to a constant value, 3 is a filter, 4 and 4a are pressure gauges, 12 is a thermostatic chamber made of a material of high heat-conductivity, e.g. aluminum, which is capable of maintaining a constant temperature therein, 5 and 8 are a laminar flow-type flowmeter and thermal-type flow controller respectively which are serially connected to each other and accommodated in the thermostatic chamber. The operating principles of the flowmeters 5 and 8A are as previously mentioned. 9 is a flow regulating device for setting and regulating the output flow of the thermal-type flow controller 8 to a constant value. The output flow can be preset at the required value indicated as a percentage (up to 100% maximum flow), to which the mass flow will be regulated. The thermal-type flow controller 8 is provided with a flow control valve and an actuating means operable by a signal from the flow regulating device 9 as will be mentioned later. 6 is a differential pressure gauge for measuring the difference $\Delta P$ between the inflow pressure $P_1$ and the outflow pressure $P_2$, 7 is an absolute pressure gauge for measuring the absolute value of the inflow pressure $P_1$. The outflow pressure $P_2$ is calculated from the differential pressure $\Delta P$ and the inflow pressure $P_1$. It is also possible to measure the outflow-side pressure $P_2$ by the absolute pressure gauge 7 and the inflow-side pressure $P_1$ is calculated from the measured values $P_2$ and $\Delta P$. 11 is a thermometer composed of a temperature sensing element such as a platinum resistance wire, thermocouple and the like for measuring the temperature of a fuel gas flowing into the laminar flow-type flowmeter 5. An absolute pressure indicator 7a and a temperature indicator 11a receive the signals from the absolute pressure gauge 7 and the thermometer 11 respectively to indicate and transfer the measured values. A computer unit 10 is used for calculating the calorific value of the fuel gas according to the equation (7) and an indicator 10a is used for indicating the calculated calorific value of the fuel gas.

A thermostatic chamber 12 made of heat-conducting material, e.g. of aluminum, is designed for accommodating therein the laminar-type flowmeter 5 and thermal-type flow controller 8 and is capable of quickly regulating the inner temperature to a constant value. A spirally wound tube 1a is provided for the exchange of heat so as to regulate the temperature of the fuel gas flowing into the laminar flow-type flowmeter 5 through the filter 3 to the inner temperature of the thermostatic chamber 12. This tube 1a is also effective to eliminate the undesirable distortion of piping of the laminar flow-type flowmeter 5 and the thermal type flow controller 8 accommodated in the thermostatic chamber 12.

The thermal-type flow controller 8 is integrally composed of a bypass type thermal flowmeter 8A and a control valve 8B for regulating the output pressure of the thermal type flowmeter to a preset value.

Figure 5:
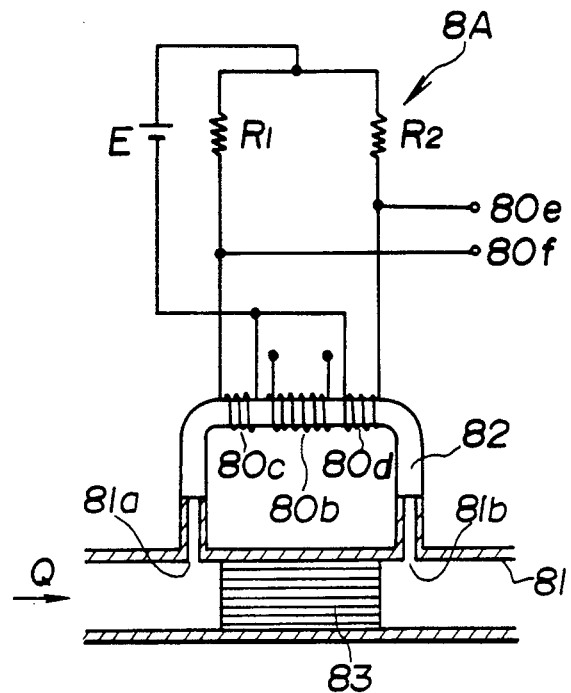
FIG. 5 is an illustration for explaining the operating principle of a bypass-type thermal flowmeter.

FIG. 5 shows a principal construction of the bypass type thermal flowmeter 8A. In FIG. 5, 81 is a mainstream pipe which allows fuel gas to flow and includes a laminar flow element 83 at the center portion thereof. 82 is a bypass pipe connected at its open ends i.e. to the ports 81a and 81b provided on the wall of the mainstream pipe respectively at the forward and the backward portions from the portion wherein the laminar flow element 83 is located. The bypass pipe 82 has a heater 80b and resistance wires 80c and 80d wound therearound. The resistances $R_1$ and $R_2$ relate to the two arms of a bridge formed by the resistance wires 80c and 80d, and a power source E is applied to the bridge. The bridge output 80e, 80f is used for measuring the mass flow through the bypass pipe 82. Since fluid flows in layers through both the bypass pipe 82 and the mainstream pipe 81, the mass flow passing through the mainstream pipe 81 is determined by the area ratio of the mainstream pipe 81 to the bypass pipe 82.

Figure 6:
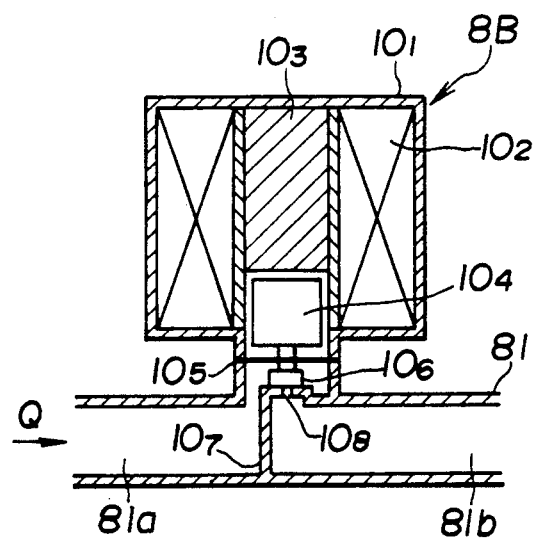
FIG. 6 is an illustration for explaining the operating principle of a control valve.

FIG. 6 shows a principal construction of the control valve 8B wherein a coil $10_2$, energized by a current corresponding to a comparison signal of the preset type flow controller 9, is housed in a casing $10_1$ with a yoke $10_3$. This coil electromagnetically drives a valve $10_6$ which cooperates with a valve seat $10_7$ having a valve port $10_8$ by which the fuel gas flow Q, passing through the main stream pipe 81, communicating with the bypass-type thermal flowmeter 8A, is divided into the upstream 81a and the downstream 81b. The valve $10_6$ is supported by a plate $10_5$ and is integrally constructed with a plunger $10_4$ which is driven electromagnetically by a current of the coil $10_2$. The plunger $10_4$ moves by a displacement at which the electromagnetic force acts on the plunger $10_4$ and the elastic force of the plate spring $10_5$ are balanced with each other.

The operation of the calorimeter embodying the present invention, which is constructed as shown in FIG. 4, is as follows:

Fuel gas from a fuel gas source (not shown) at a specified pressure flows in the direction of arrow F in the stream pipe 1 and moves through the reducing valve 2, by which its pressure is reduced to a substantially constant value and then passes through a filter 3 for cleaning off particles and then flows into the thermostatic chamber 12 wherein the fuel gas temperature is kept at the temperature T until the fuel gas flows into the laminar flow-type flowmeter 5 through a spiral tube 1a. The inflow pressure $P_1$ of the laminar flow-type flowmeter 5 is detected as an absolute pressure. The measured values of the inflow pressure $P_1$ and the differential pressure $\Delta P$ are input into the computer unit 10 which calculates the outlet pressure $P_2$ from the input values. In this case the volume flow of the fuel gas passing through the laminar flow-type flowmeter 5, which is expressed by the equation (2), represents the flow of the fuel gas in its normal state at the temperature T, the absolute inlet pressure P1, the outflow pressure $P_2$ and the differential pressure $\Delta P$. Since the mass flow of the fuel gas measured by the thermal-type flow controller 8 accurately corresponds to the volume flow of the fuel gas in the normal state, the equation (3) is satisfied and the calorific value H of the fuel gas can be indicated on the indicator 10a as a value being inversely proportional to the differential pressure $\Delta P$ of the laminar flow-type flowmeter 5 calculated from the known pressures $P_1$ and $P_2$ in the equation (7).

Figure 7:
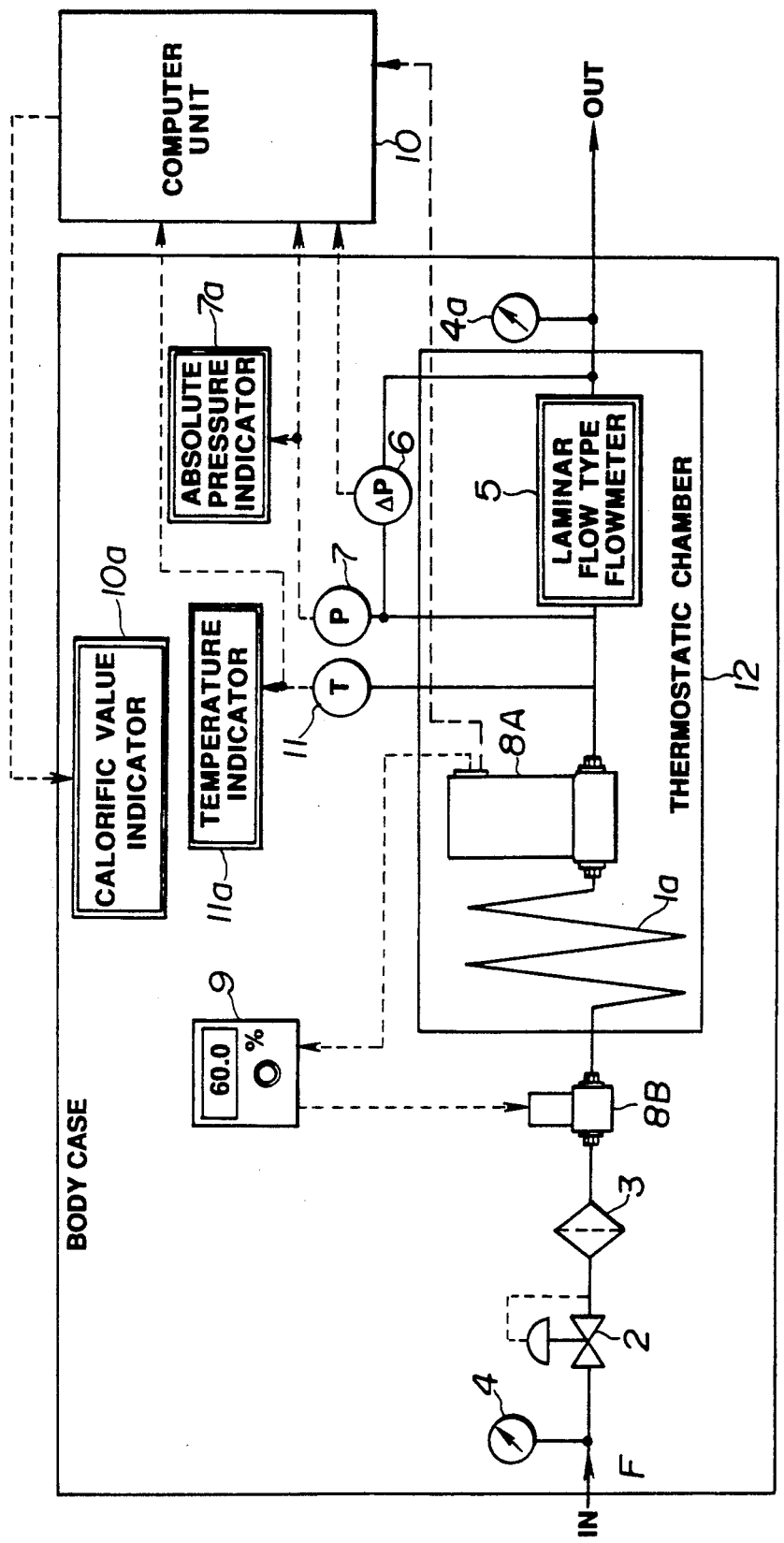
FIG. 7 shows another example of a construction of a calorimeter embodied in the present invention.

FIG. 7 shows another calorimeter embodied in the present invention. The thermal-type flow controller 8 indicated in FIG. 4 is divided into the thermal-type flowmeter 8A and the control valve 8B which is separately located outside of the thermostatic chamber 12 so as to prevent the inner temperature of the thermostatic chamber 12 from varying due to the heating of the coil $10_2$ for exciting the control valve. Although the laminar flow-type flowmeter 5 and the thermal-type flowmeter 8A in FIG. 7 differ from those shown in FIG. 4 by their location in relation to the direction of the fuel gas flow, it is also possible to locate the thermal type flowmeter 8A downstream from the laminar flow-type flowmeter 5 but outside of the thermostatic chamber.

As is apparent from the foregoing, a calorimeter, according to the present invention, is capable of measuring the calorific value of a mixed fuel gas with a higher accuracy and by simpler means with no effect or variation in the flow conditions by virtue of the possibility of converting the volume of flow of the fuel gas, measured by a laminar flow-type flowmeter, into the flow in normal conditions.

According to the present invention it is also possible to provide a simple and low-cost calorimeter which by virtue of the adoption of a thermostatic chamber that is a good heat conductor with a reduced variation of the inner temperature, is capable of stabily measuring the calorific values of the mixed fuel gas and is suitable for use as an auxiliary measuring means for a standard calorimeter.

What is claimed is:
1. A calorimeter comprising:
laminar flow type flowmeter means for measuring the flow rate of a fuel gas passing therethrough as a value proportional to the difference between the pressures of a laminar flow of the fuel gas at an inlet and an outlet of said laminar flow type flowmeter means, said laminar flow type flowmeter means including differential pressure gauge means for sensing a differential pressure of the fuel gas between the inlet and outlet of the laminar flow type flowmeter means and for producing a differential pressure output signal in response thereto;

thermal-type flowmeter means for measuring a flow rate of said fuel gas in proportion to a detected temperature differential between two spaced positions of said thermal-type flowmeter means, and for producing an output signal in response thereto, said thermal-type flowmeter means including:

heating means for heating said fuel gas passing through said thermal-type flowmeter means, and differential temperature sensing means for detecting a differential between the temperature of said fuel gas at a point before said heating means and the temperature of said fuel gas at a point after said heating means, and for producing said output signal in response thereto;

pre-set type flow controller means for maintaining the output of the thermal-type flowmeter means at a constant value for fuel gas passing therethrough;

thermometer means for sensing the temperature of the fuel gas flowing into the laminar flow type flowmeter means and for providing a temperature signal in response thereto;

absolute pressure gauge means for sensing the absolute pressure of the fuel gas flowing into or out of the laminar flow-type flowmeter and for producing an absolute pressure signal in response thereto;

computer means for calculating the calorific value of the fuel gas as a value that is inversely proportional to the differential pressure of the fuel gas between the inlet and outlet of the laminar flow type flowmeter means, in response to said absolute pressure signal, said differential pressure signal and the output signal from said thermal-type flowmeter means.

2. A calorimeter as claimed in claim 1, wherein the thermal-type flowmeter means includes a mainstream pipe having at least one laminar element therein, a tube forming a bypass line of the mainstream pipe and containing said heating means and said differential temperature sensing means for sensing the difference between the temperatures of the fuel gas flow before and after said heating means.

3. A calorimeter as claimed in claim 1, wherein the laminar flow type flowmeter means and the thermal type flowmeter means are serially connected to each other and accommodated in a thermostatic chamber made of aluminum.

4. A calorimeter as claimed in claim 3, wherein said preset type flow controller means includes regulating valve means serially connected to the thermal-type flowmeter means for maintaining the output of the thermal type flowmeter means at said constant value, said regulating valve means being placed outside of the thermostatic chamber.

* * * * *